United States Patent
Tegel et al.

(10) Patent No.: US 12,239,752 B2
(45) Date of Patent: Mar. 4, 2025

(54) EXPOSURE AND DECONTAMINATION CAROUSEL

(71) Applicants: Robert G. Tegel, Orangeville, IL (US); Turan Erdogan, Kingston, MA (US); David H. Adams, Chesterfield, MO (US)

(72) Inventors: Robert G. Tegel, Orangeville, IL (US); Turan Erdogan, Kingston, MA (US); David H. Adams, Chesterfield, MO (US)

( * ) Notice: Subject to any disclaimer, the term of this patent is extended or adjusted under 35 U.S.C. 154(b) by 846 days.

(21) Appl. No.: 17/471,515

(22) Filed: Sep. 10, 2021

(65) Prior Publication Data

US 2022/0088242 A1 Mar. 24, 2022

Related U.S. Application Data

(60) Provisional application No. 63/080,823, filed on Sep. 21, 2020.

(51) Int. Cl.
*A61L 2/10* (2006.01)
*B08B 7/00* (2006.01)

(52) U.S. Cl.
CPC ............ *A61L 2/10* (2013.01); *A61L 2202/11* (2013.01); *A61L 2202/122* (2013.01); *A61L 2202/14* (2013.01); *A61L 2202/16* (2013.01); *B08B 7/0035* (2013.01)

(58) Field of Classification Search
CPC .... A61L 2/10; A61L 2202/14; A61L 2202/16; B08B 7/0035; B08B 11/02
See application file for complete search history.

(56) References Cited

U.S. PATENT DOCUMENTS

| | | |
|---|---|---|
| 4,112,124 A | 9/1978 | Jarvis |
| 8,143,596 B2 | 3/2012 | Yerby |
| 9,265,849 B2 | 2/2016 | Kerr |
| 9,295,741 B2 | 3/2016 | Yerby |
| 9,566,819 B2 | 2/2017 | McDowell |
| 9,675,721 B2 | 6/2017 | Dayton |
| 10,272,167 B2 | 4/2019 | Starkweather et al. |
| 10,357,583 B2 | 7/2019 | Dayton |
| 10,376,605 B1 * | 8/2019 | Majdali ............... A61L 2/10 |
| 10,478,515 B2 | 11/2019 | Shur et al. |
| 10,646,603 B2 | 5/2020 | Shur et al. |
| 2005/0230640 A1 * | 10/2005 | Loda .................. G21K 5/10 250/455.11 |

(Continued)

FOREIGN PATENT DOCUMENTS

GB 419929 11/1934

Primary Examiner — Sean E Conley
Assistant Examiner — Eric Talbert
(74) Attorney, Agent, or Firm — Louis S. Horvath

(57) ABSTRACT

An apparatus for exposing an article to radiant energy has a rotating carousel having an article support in a support sector defined between a first energy-blocking feature of the rotating carousel and a second energy-blocking feature of the rotating carousel. An actuator is energizable to rotate the carousel and to revolve the article support along a circular transport path. An enclosure has a stationary hood that defines an enclosed sector of the transport path and an unenclosed sector of the transport path. There is at least a first radiant energy source energizable to direct the radiant exposure energy toward the carousel along the enclosed sector of the transport path.

20 Claims, 18 Drawing Sheets

(56) References Cited

U.S. PATENT DOCUMENTS

2009/0032527 A1    2/2009  Lee et al.
2012/0138822 A1    6/2012  Leben
2013/0171037 A1    7/2013  Im
2015/0115172 A1    4/2015  Freue et al.
2016/0324997 A1*  11/2016  Dayton ..................... A61L 2/10
2017/0368215 A1*  12/2017  Shatalov ................ G01G 19/52

\* cited by examiner

EXPOSURE AND DECONTAMINATION CAROUSEL

CROSS REFERENCE TO RELATED APPLICATIONS

This application claims the benefit of U.S. Provisional Application Ser. No. 63/080,823, entitled "EXPOSURE AND DECONTAMINATION CAROUSEL", in the names of Robert G. Tegel et al., filed 21 Sep. 2020 and incorporated herein in its entirety.

FIELD

The present disclosure generally relates to apparatus and methods for radiation exposure, such as methods and apparatus using ultraviolet (UV) radiation for exposing portions of an object.

BACKGROUND

A pathogen or other infectious agent can be conveyed between persons by means of a carrier object, such as personal article handled or worn by a subject. Personal objects, particularly those carried or worn by a subject, are acknowledged to be likely carriers for pathogens, often affording a ready path for disease transmittal from one subject to another.

Various strategies are used to counteract pathogen spread, such as sanitizing articles touched, worn, or otherwise subject to contact, or near-contact, with any potentially infected or exposed person. Thus, for example, a number of different apparatus may use sanitizing fluids to immerse, surround, or envelop the article, or may use radiant energy directed toward the article from various angles and at energy levels calculated to decontaminate the article.

One fairly effective approach sanitizes the article using Ultraviolet light (UV), particularly light in the UV-C range (nominally, with wavelengths in the range of about 100 to 280 nm). UV-C exposure systems have been used in industrial applications, such as for curing adhesives or coatings treatments, as well as in food processing and other areas for manufacture and packing of sterilized items.

Solutions to the problem of providing effective use of UV-C for surface sanitizing personal articles would have a number of features, including the following:

(i) Hands-free operation. Operation requiring minimal surface contact would help to prevent unintended contamination when using the device.
(ii) Minimized likelihood and impact of operator error. Straightforward operation can help to minimize the need for operator knowledge, training, or decision-making in sanitizing personal items. The ideal solution should allow operation by the end-user. Adjustment devices and approaches should be straightforward and easily accessible, allowing the operator to tune the sanitizer to achieve appropriate exposure levels for different types of articles.
(iii) Containment of the radiation to avoid operator exposure. The high-energy UV-C radiation can be harmful for any living organism. While interlocks and similar types of devices for temporarily disabling power can be provided, it would be particularly advantageous to provide apparatus and methods that inherently shield the operator from direct access to exposure components and, where possible, even from visibility of the exposure chamber. Contact with exposure components can shorten component lifetimes: many types of high-energy UV exposure lamps can exhibit reduced effectiveness and reduced bulb lifetime due to contact with skin oils, for example.
(iv) Efficient radiation pattern. Exposure is a factor of both timing and intensity. Intensity decreases significantly as a function of distance from the radiant source. Efficiency is also enhanced by providing light over a larger range of incident angles.
(v) Compact size and reasonable cost.

Conventional solutions fail to satisfy at least some of the features (i)-(v) listed hereinabove. Another difficulty with existing UV exposure systems relates to bulb life and use. UV bulbs can require an amount of warm-up time before reaching rated power levels. Continuous power cycling, needed, for example, with systems that allow operator access to the exposure chamber for loading and unloading, can degrade bulb performance and shorten bulb life.

Apparatus currently used for article sanitizing are typically bulky and sized for industrial use, not packaged for ease of use by untrained personnel, such as a walk-up crowd at an airport, school, or manufacturing facility. Instead, conventional systems can require significant setup and operation training. While existing UV exposure systems typically provide interlocks and other solutions for disabling radiation, such as when chamber doors are open, they still permit access to the sterilization chamber itself and present risks of component contact and surface degradation. Allowing operator access to the exposure chamber risks operator contact with chamber surfaces, which are often treated to maximize UV reflection. Further, typical solutions may sanitize multiple articles at the same time, with limited ability to track individual articles and allowing sanitized articles to be unattended for considerable amounts of time.

Thus, it can be appreciated that there would be advantages to a UV exposure apparatus that overcomes the limitations of existing sanitizing and curing equipment and meets the requirements given above.

SUMMARY

The Applicants address the problems listed in the background section for providing controlled UV exposure to articles for sanitizing and for other processes using high-energy light. Embodiments of the present disclosure provide a UV exposure solution that addresses requirements (i) through (v) listed previously in the background section.

According to an embodiment of the present disclosure, there is provided an apparatus for exposing an article to radiant light, comprising:
- a rotating carousel having an article support in a support sector defined between a first energy-blocking feature of the rotating carousel and a second energy-blocking feature of the rotating carousel;
- an actuator energizable to rotate the carousel and to revolve the article support along a circular transport path;
- an enclosure having a stationary hood that defines an enclosed sector of the transport path and an unenclosed sector of the transport path; and
- at least a first radiant energy source energizable to direct the radiant exposure energy toward the carousel along the enclosed sector of the transport path.

DRAWINGS

FIGS. 3A, 3B, 3C, and 3D show perspective exploded views of the exposure carousel at different rotational positions.

Figure 4A:
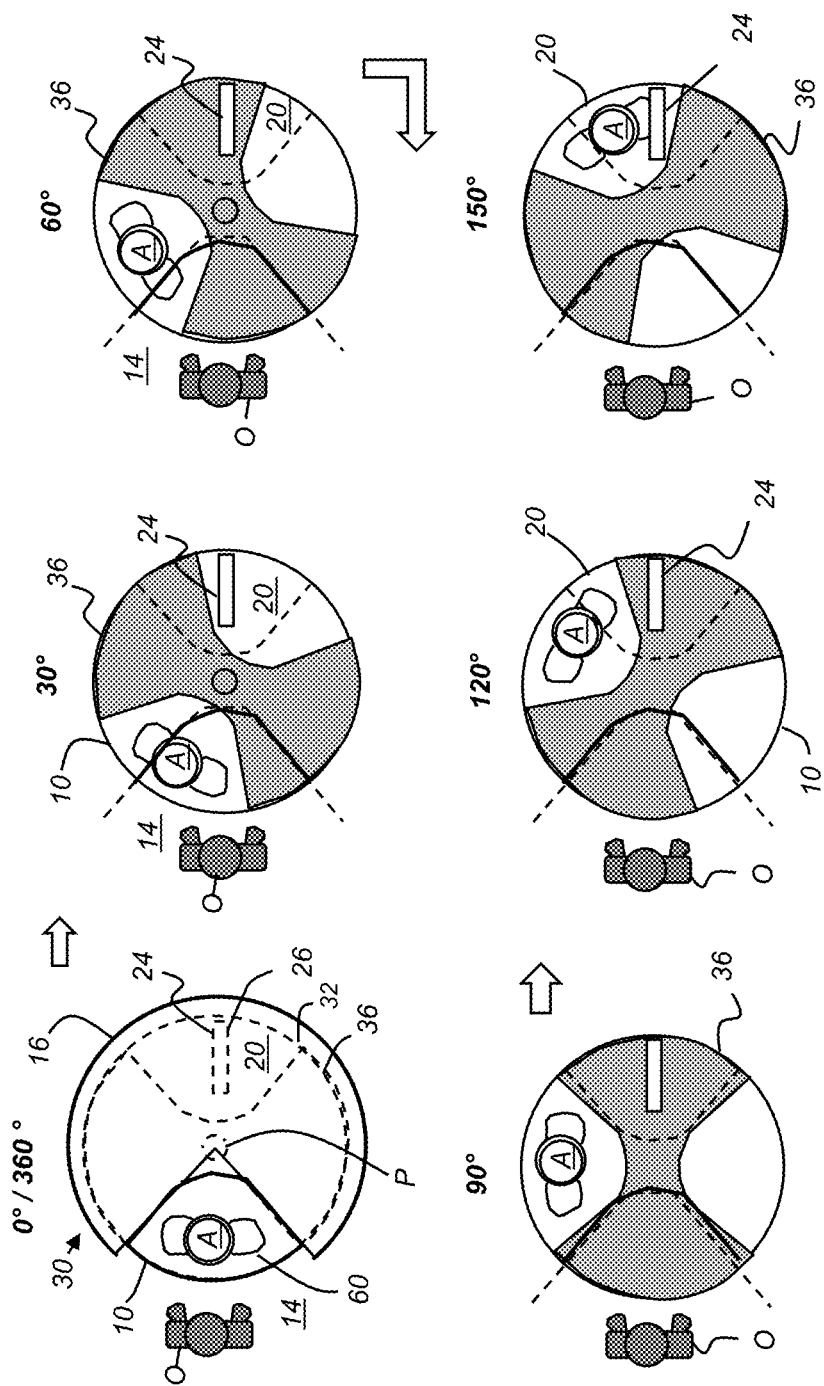
Figure 4B:
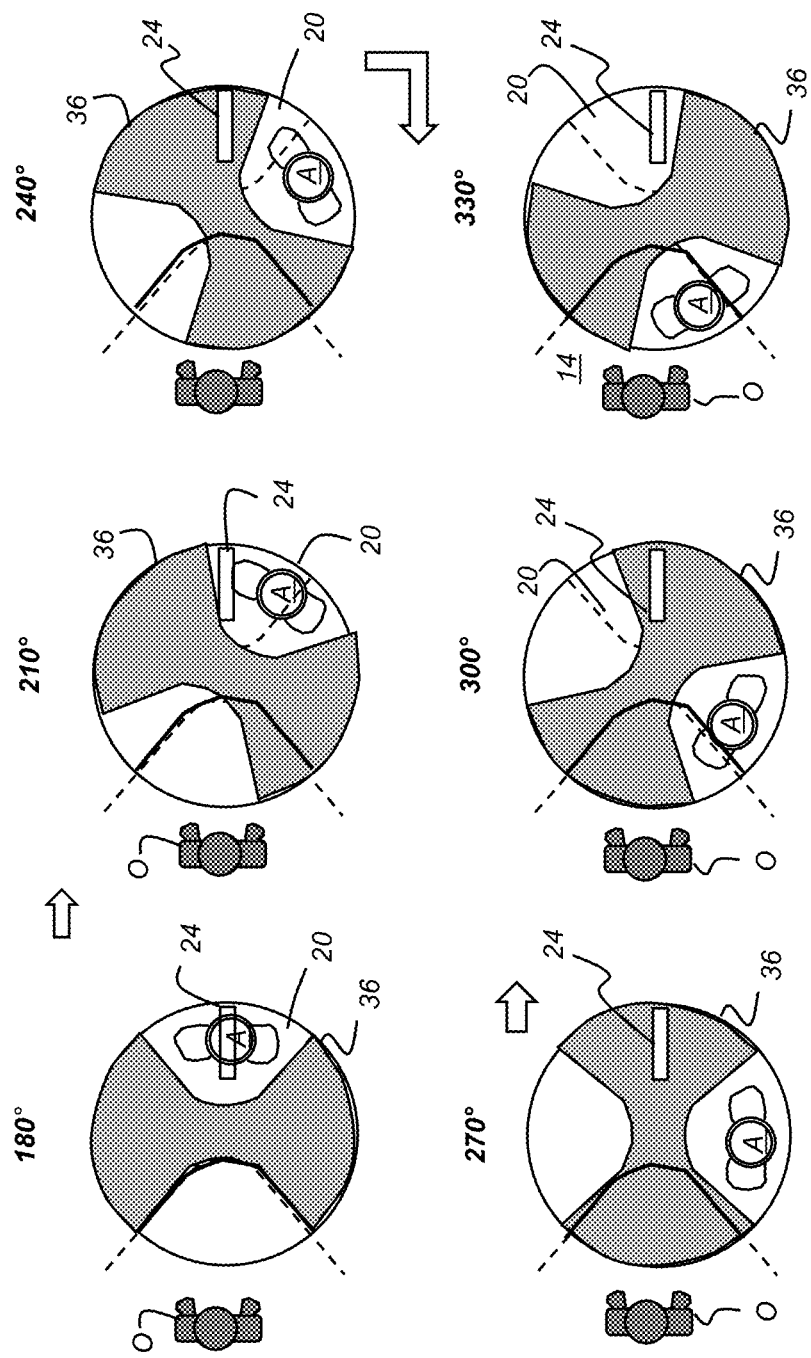

FIGS. 4A and 4B are top view schematics showing the exposure sequence in summary form.

Figure 5B:
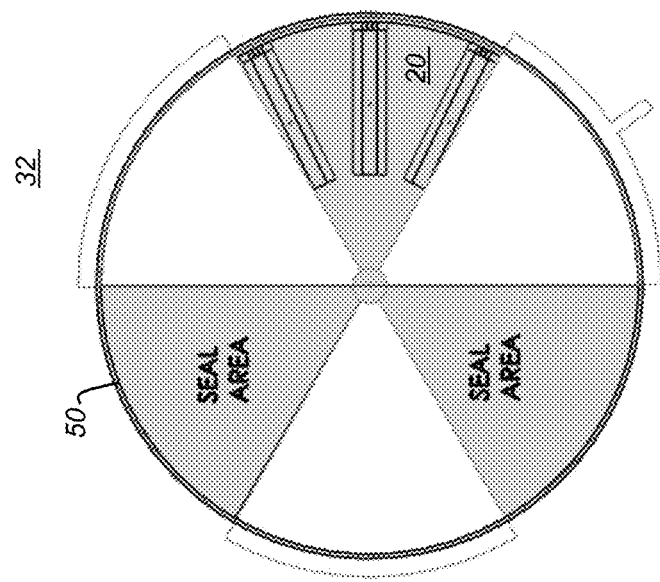
Figure 5A:
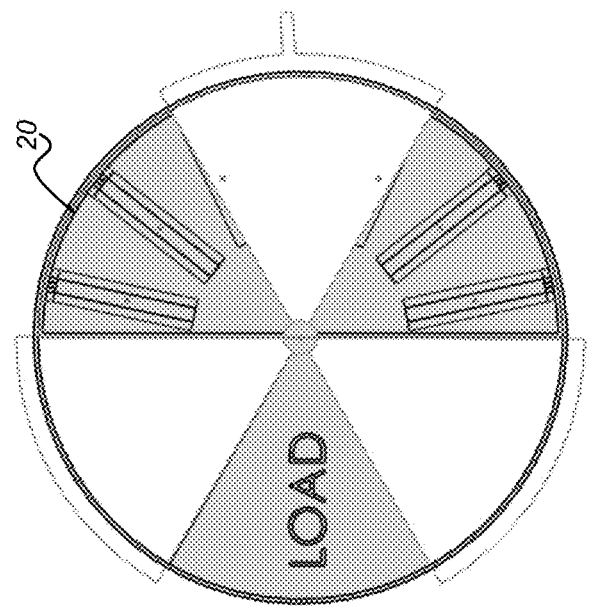

FIGS. 5A and 5B are top view schematics showing an embodiment having multiple sectors for loading articles for exposure.

Figure 5D:
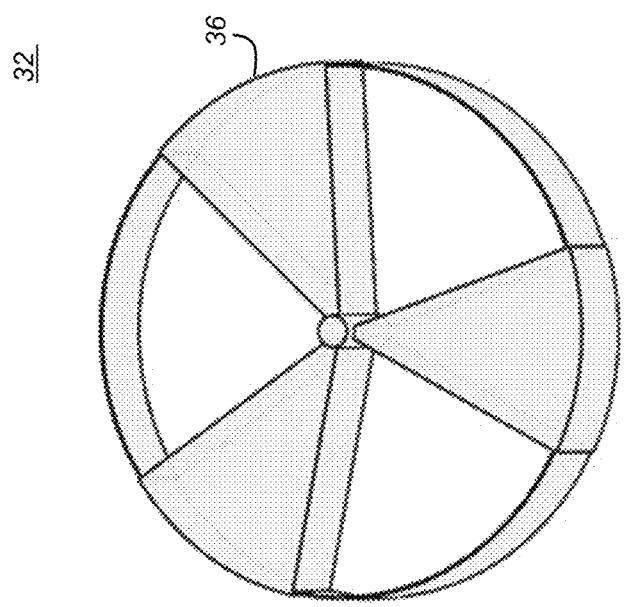
Figure 5C:
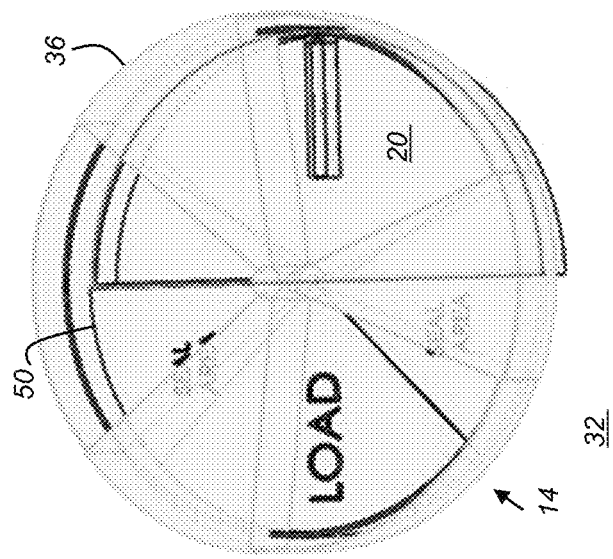

FIGS. 5C and 5D are perspective views showing relative position of the carousel to stationary components according to an alternate embodiment.

Figure 6:
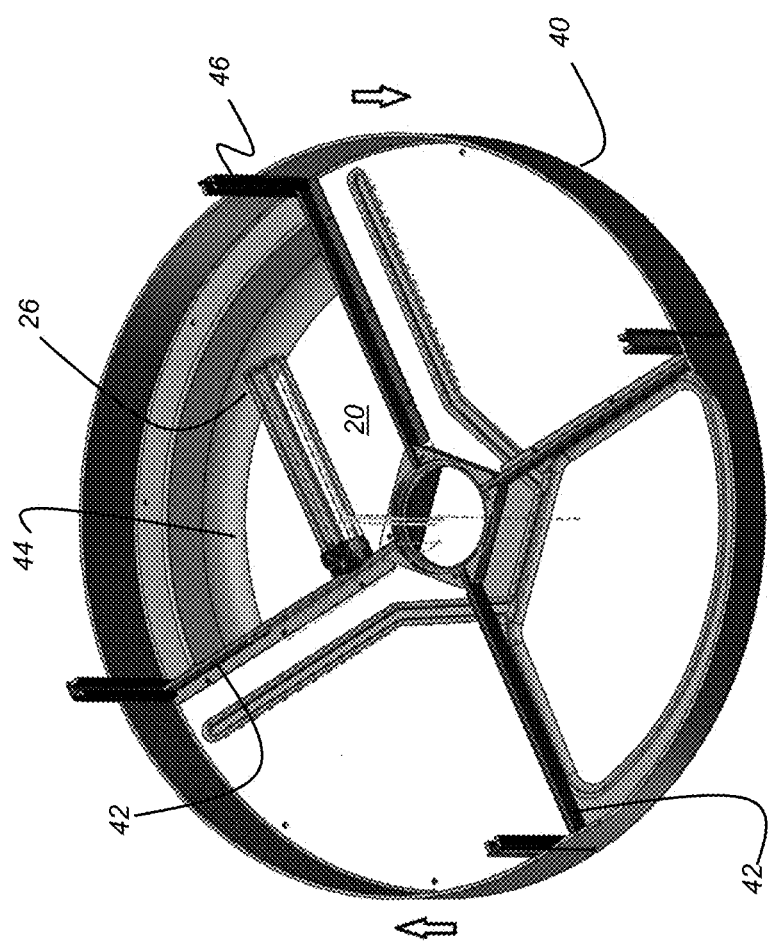

FIG. 6 is a perspective view showing components forming the base of the exposure carousel and bottom portion of the exposure chamber.

Figure 7:
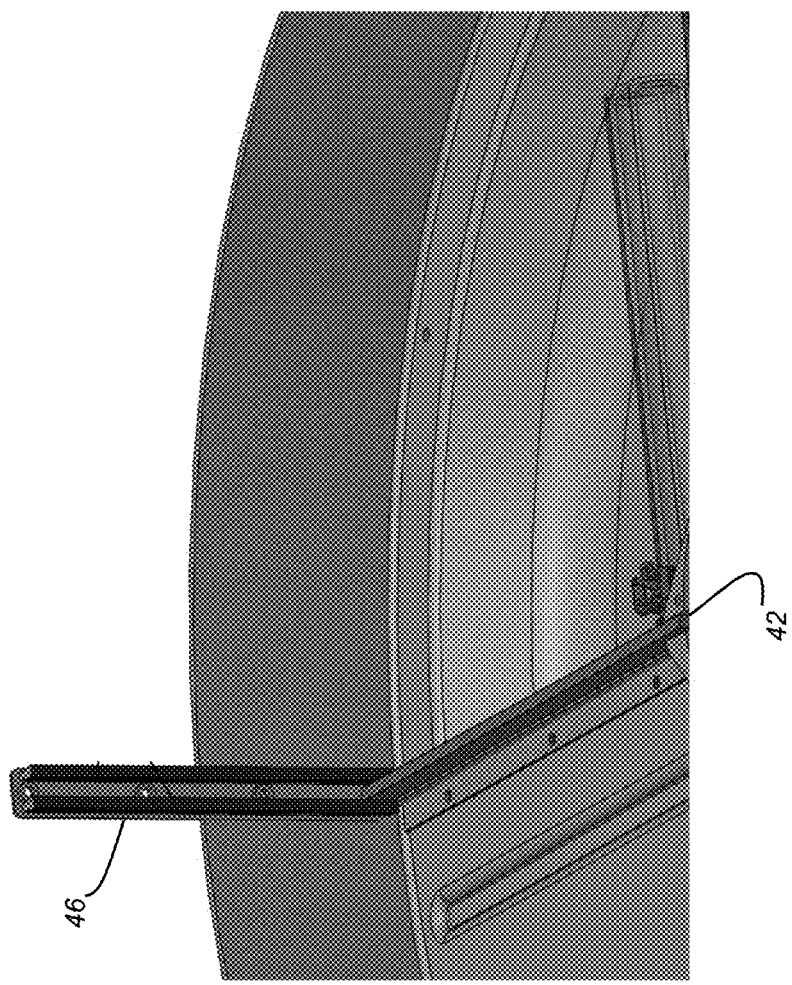

FIG. 7 shows perimeter seal components of the indexing apparatus.

Figure 8:
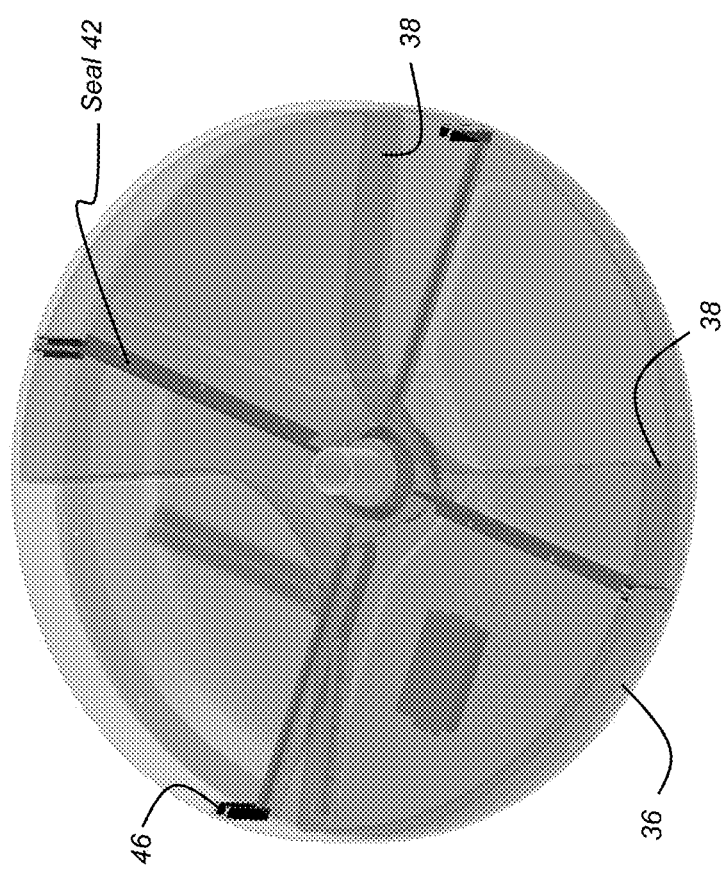

FIG. 8 is a perspective view that shows lower seal position relative to the sealing shroud at one angular position, according to an embodiment.

Figure 9:
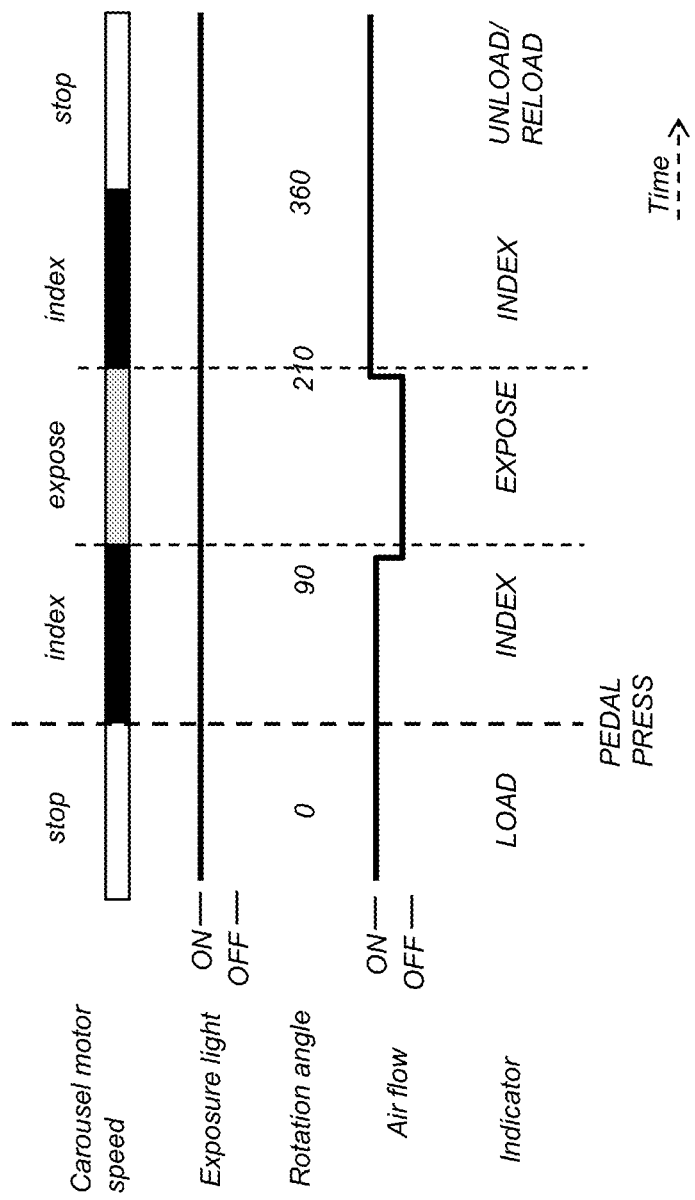

FIG. 9 is a graph showing an exemplary timing chart for various phases of operation of an exposure apparatus.

Figure 10A:
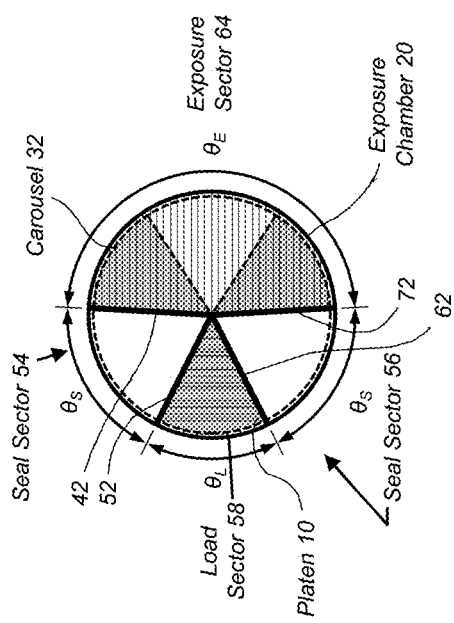
Figure 10B:
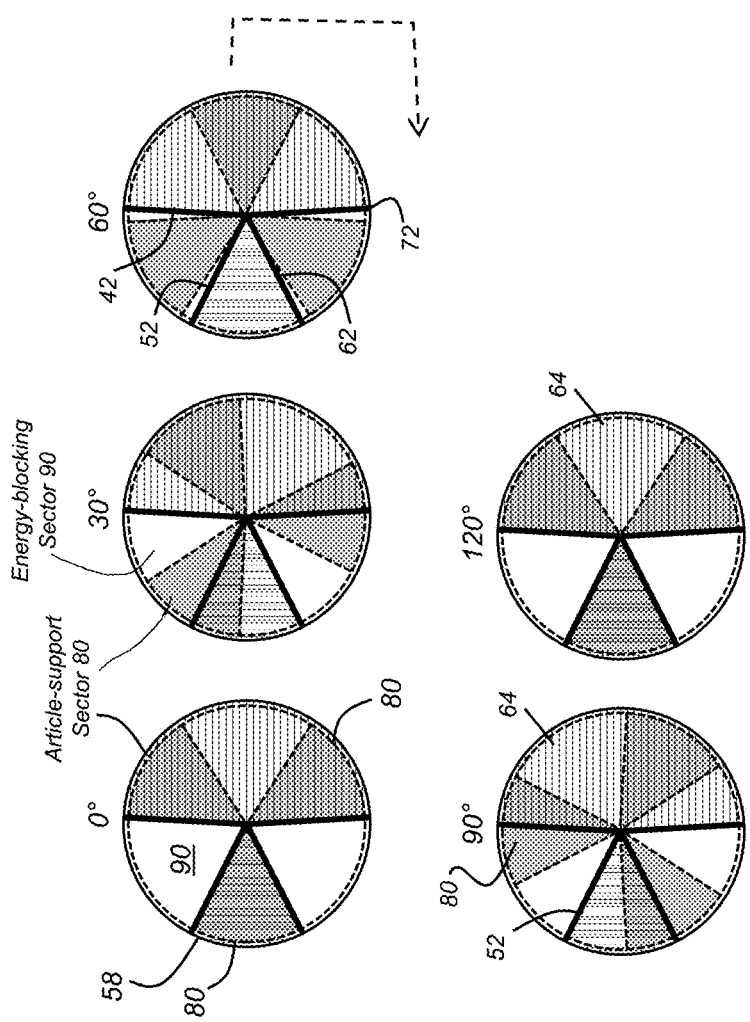
Figure 10C:
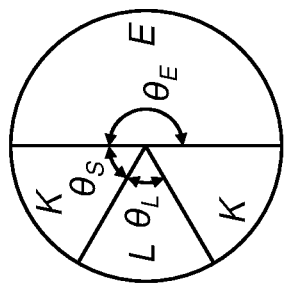
Figure 10C:
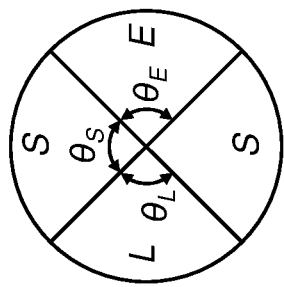

FIGS. 10A-10C show some of the principles applicable for expanding the number of loading areas for user convenience.

DETAILED DESCRIPTION

The following is a detailed description of the preferred embodiments of the disclosure, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

The terms "user", "operator", and "subject" may be used interchangeably in the present disclosure, and relate to any individual who introduces or removes an article on the apparatus of the present disclosure for exposure processing.

An embodiment of the present disclosure provides apparatus for controlled UV exposure of articles, such as personal articles, such as for sanitizing to render surfaces of the article substantially free of pathogens. It can be noted that the disclosed apparatus can have broader application to any of a number of functions that use exposure to UV or other high-energy radiant sources and can include various industrial applications, such as for curing various types of polymer materials, such as adhesives, for example. However, without limitation, the description that follows illustrates the apparatus structure, components, and functions with relation to an embodiment for sanitization as one example that has particular utility.

Figure 1:
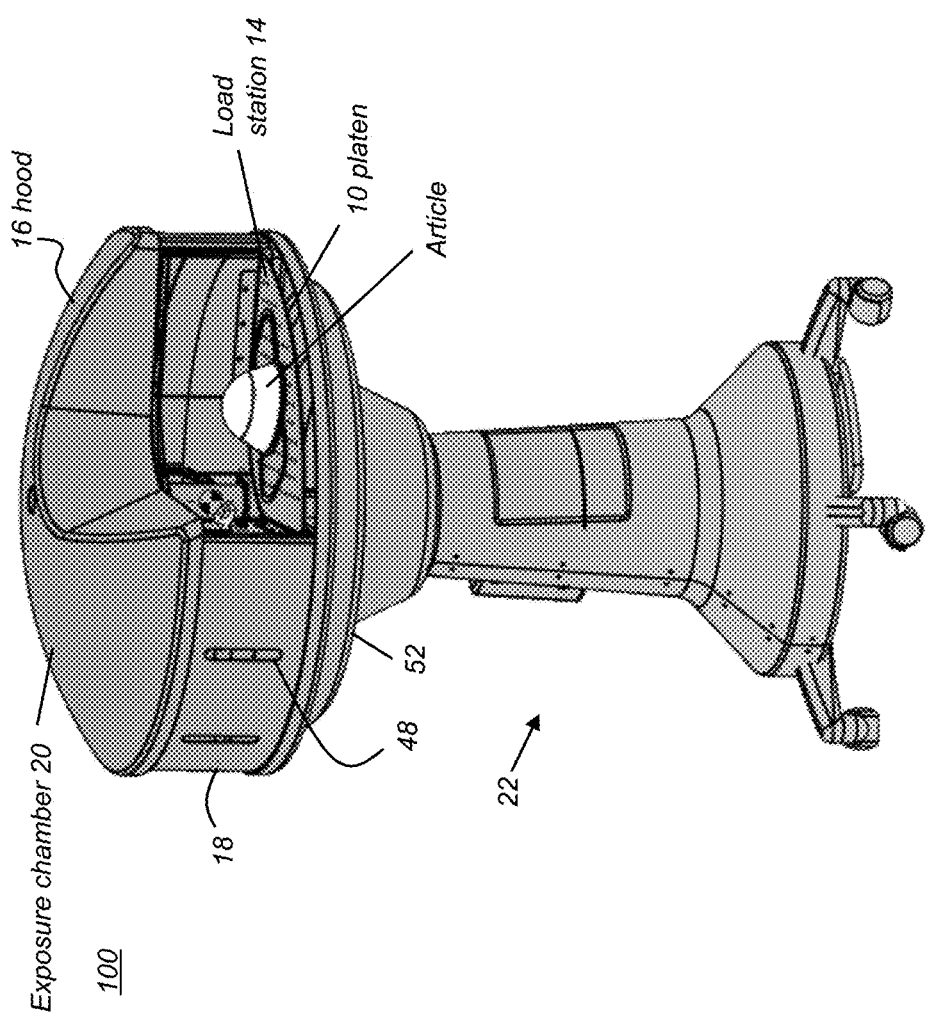
FIG. 1 is a perspective view that shows an apparatus for UV exposure according to an embodiment.

The perspective view of FIG. 1 shows an apparatus for UV exposure of an article according to an embodiment. For illustration, the article is shown as a face mask; in practice, exposure apparatus 100 can be used for sanitizing any of a number of types of personal devices. A UV exposure apparatus 100 operates as a carousel, indexing, by rotation, an article on a platen 10 into and through an internal exposure chamber that is enclosed therein. A stationary hood 16 provides part of an enclosure for the exposure source. Hood 16 covers upper portions of an exposure chamber 20 and is coupled to a surface 18 that extends about sides of chamber 20 and seals against a lower casing or bottom cover, casing 52; optionally, hood 16 can be a single unit that also encloses the sides and provides the function of surface 18.

The carousel arrangement of FIG. 1 separates the operator from exposure hardware, isolating exposure components that are housed within an internal exposure chamber 20 from contact with or visibility to the operator throughout the exposure cycle, at each rotational angle of the carousel platen 10. A pedestal or base 22 supports chamber 20 and can include control, power, and actuator components, as well as components for transport, for example.

With the FIG. 1 configuration, there is no operator access to the exposure chamber 20 at any point in the exposure cycle. Maintaining the exposure chamber 20 inaccessible to the user and fully light-tight helps to minimize bulb power cycling and also to minimize likelihood of inadvertent exposure to the user as well as to prevent potential contact with UV light sources or inner chamber surfaces, which could shorten bulb life or otherwise degrade system performance. Energy-blocking features provided on and surrounding the carousel help to define a load sector and seal the exposure energy within the UV exposure apparatus 100. Operator activity consists in loading and unloading articles onto or from a rotatable platen for curing or sanitizing, in initiating the exposure cycle, and, optionally, in adjusting platen rotation speed or direction, or making some other adjustment related to exposure dose. Operator activity for routine apparatus operation can be hands-free, as described subsequently.

Figure 2A:
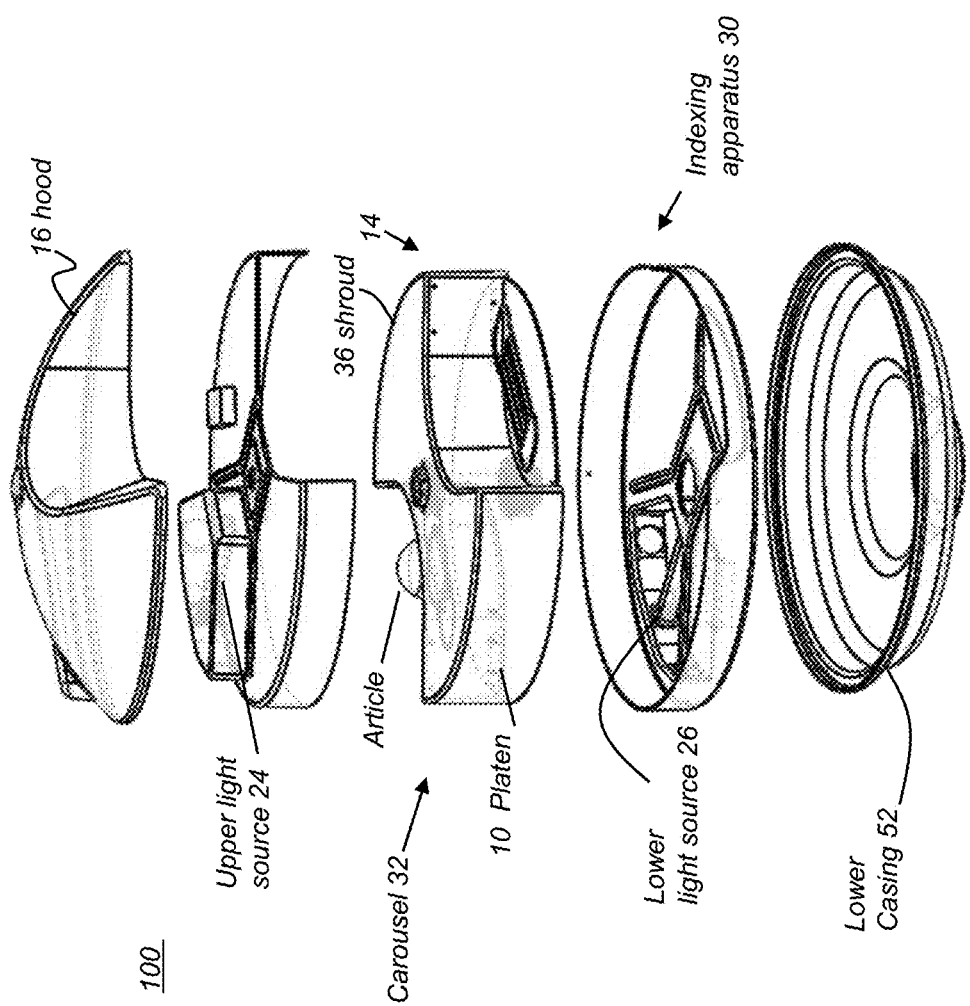
FIG. 2A is a partially exploded view showing apparatus components for UV exposure.
Figure 2B:
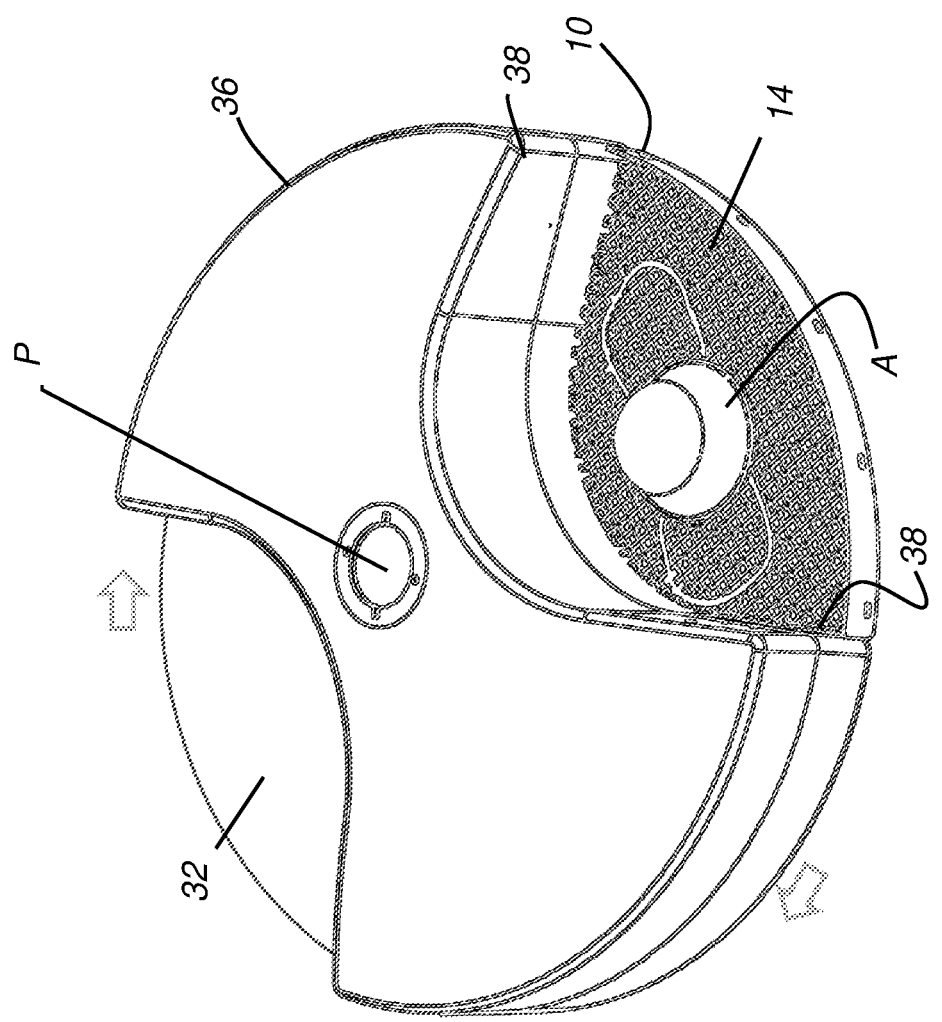
FIG. 2B is a perspective view of the carousel assembly, including the exposure platen.
Figure 2C:
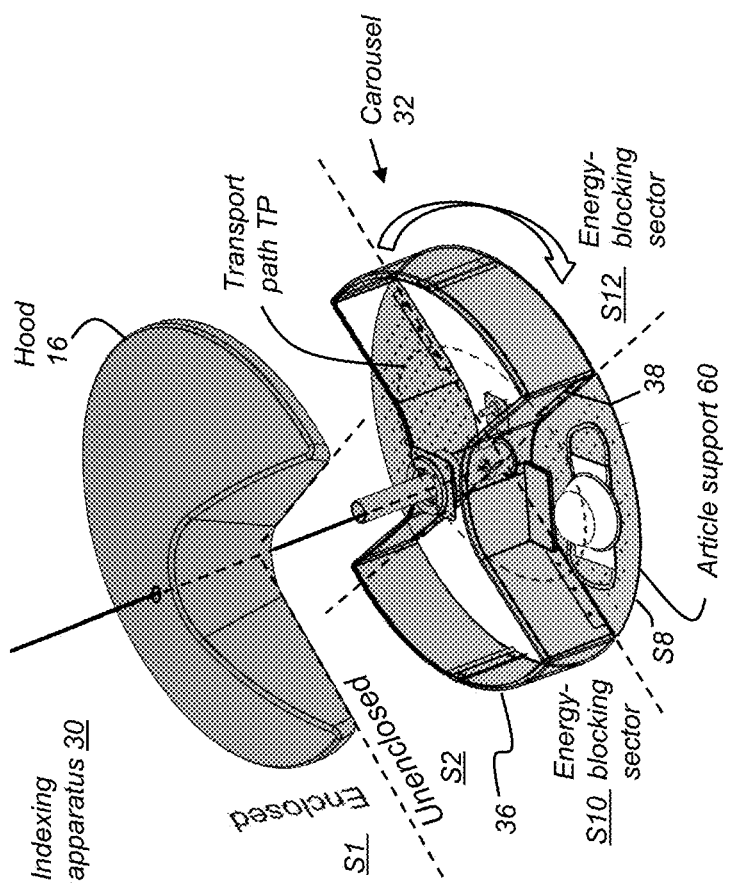
FIG. 2C is an exploded view showing the arrangement of fixed and rotatable sectors defined by system indexing geometry.

FIGS. 2A, 2B, and 2C show the structure of related elements of apparatus 100 that provide carousel operation for article exposure. FIG. 2A is a partially exploded view of apparatus 100, showing components of an indexing apparatus 30 that revolves the article along a circular transport path. A rotary exposure carousel 32 is driven by an actuator (not shown) such as a motor that rotates a drive shaft or otherwise provides rotational indexing with reference to a central pivot point P. As shown for a carousel 32 embodiment presented in FIG. 2B, a protective sealing shroud 36, as a light energy-blocking element, is coupled to a platen 10 for rotation about the pivot P. In the exemplary embodiment shown, energy-blocking surfaces 38 of sealing shroud 36 are features that define a sector for article A support in load station 14. Thus, for protection of the human operator, as the sealing shroud 36 revolves with the carousel 32, a continuous light-tight seal about exposure chamber 20 is maintained throughout carousel 32 rotation. Advantageously, apparatus 100 provides an exposure system needing no door or door-related interlock devices for exposure of an article. Apparatus 100 can run continuously, allowing the operator(s) to load and unload articles as the carousel slowly rotates.

The schematic diagram of FIG. 2C shows the indexing apparatus geometry that allows exposure of personal articles without operator contact to the apparatus or operator exposure to the radiant light energy that is used. The travel path of the article to be exposed is along a circle with indexing provided for travel in either the clockwise or counterclockwise direction. The indexing apparatus 30 uses an arrangement of sectors; exposure is effected by an alignment of movable sectors of the carousel with fixed sectors of the enclosure.

Geometrically, a sector is the area of a circle defined between any two radial lines and the intercepted arc. Expressed more simply, a sector is a pie-slice-shaped portion of a circle. From a general and practical aspect, the mechanical features of indexing apparatus 30 define and use two sets of sectors, one movable (on the rotating carousel), the other fixed (by the stationary hood and other components), and use the relationship of the movable sectors to the fixed sectors to provide the various stages of the exposure function. Pivot P serves as the center point for both movable and fixed sectors. Energy-blocking features for containment of the radiant energy can be provided both on rotating components of the carousel, such as on platen 10, and on surrounding stationary components, such as along edges of hood 16.

Rotating carousel 32 is segmented into various sectors for article support in loading, transport, exposure and unloading, as well as one or more sectors providing energy-blocking features. According to an embodiment shown in FIG. 2C, carousel 32 has at least two movable sectors that are configured to revolve about pivot P: one sector provides an article support, such as a mat, holder, platform, or base that is intended to hold the article to be exposed. The article-support sector is bounded by surface 38 features of one or more movable energy-blocking sectors, shown as sectors S10 and S12 in the example of FIG. 2C. Energy-blocking sectors are configured to contain exposure energy within the exposure apparatus 100 as the carousel 32 rotates and to shield the operator from inadvertent exposure or contact with the exposure chamber, at every rotational angle as the article moves in its circular transport path TP.

In the exemplary embodiment shown in FIG. 2C there can be two movable article-support sectors S8, each of which spans about a 90-degree angle, and two movable energy-blocking sectors S10 and S12, each of which also spans about 90 degrees of angle. However, it should be clear that other configurations are possible with the same 90 degree article-support sector, such as a single 90-degree movable article-support sector and a single 270-degree movable energy-blocking sector, or four approximately 90-degree movable article-support sectors and four approximately 0-degree movable energy-blocking sectors, wherein surfaces of the energy-blocking sectors on the carousel provide the energy-blocking features that bound or define the article support sectors. According to an alternate embodiment of the present disclosure, the energy-blocking sectors can be in the form of narrow walls or dividers, each of which spans a very small angular range. Seals can be affixed to the edges of each wall or divider.

Circular transport path TP passes within the stationary enclosure. Along path TP, the stationary enclosure has two sectors that have fixed positions, as defined by the "cutout" in hood 16. As FIG. 2C shows, hood 16 covers an enclosed sector 51 that extends over most of circular transport path TP, such as about 270 degrees in the non-limiting example illustrated. A small portion of the path TP, a sector S2 that is unenclosed, corresponds to a loading station, sized to accommodate article support 60 as carousel 32 rotates support 60 into the corresponding angular range in its cycle.

Thus, it can be seen that the exposure cycle is based on the relationship of the moving carousel sectors, S8, S10, S12 that revolve about pivot P to the stationary enclosure sectors S1, S2 that are centered about pivot P.

Exposure Chamber

FIGS. 3A-3D show aspects of the exposure cycle as it executes beneath hood 16, with fixed-position components and revolving components according to an embodiment of the present disclosure. Carousel 32 features are slightly different from that shown in FIG. 2B, but follow the same sector model described previously. As shown in the partial perspective schematic views of FIGS. 3A-3D, exposure chamber 20 has an upper radiant energy source 24, which can be located near the inner surface of hood 16, and a lower radiant energy source 26, disposed near the bottom of chamber 20. Indexing apparatus 30 is configured to convey platen 10 through chamber 20, between radiant energy sources 24 and 26, in order to obtain broad-surface exposure of both top and bottom surfaces of the article as the article moves along. Conveyance of the articles through the sector that lies between upper and lower radiant energy sources 24 and 26 and forms exposure chamber 20 exposes the articles to UV light incident from a substantial range of different angles. Rotational speed, and the sector arc length or angular extent of the arc traveled within the exposure chamber 20, along with light intensity and duration, whether pulsed or continuous, determine the actual exposure time and energy that is delivered.

Radiant energy sources 24 and 26 can be disposed to be perpendicular with respect to a plane parallel to the platen 10 or can extend in other directions.

Exposure effectiveness can be further enhanced by reflection from side wall and other inner surfaces within and near exposure chamber 20. Reflective coatings can be provided to one or more inner surfaces to increase efficiency as well as to provide light from multiple angles. The reflective surfaces may provide specular (mirror-like) reflection, diffuse reflection (such that light at a particular incident angle reflects or scatters into a substantial range of angles), or some combination of both specular and diffuse reflection.

Exposure effectiveness can also be enhanced by introducing one or more gases or other fluids into exposure chamber 20, such as at one or more intervals during the exposure cycle. The fluids introduced can be sanitizing, reactive, or inert.

Radiant energy can be UV-C, as described previously, or other light energy that is effective for exposure.

Operation of Indexing Apparatus

Figure 3A:
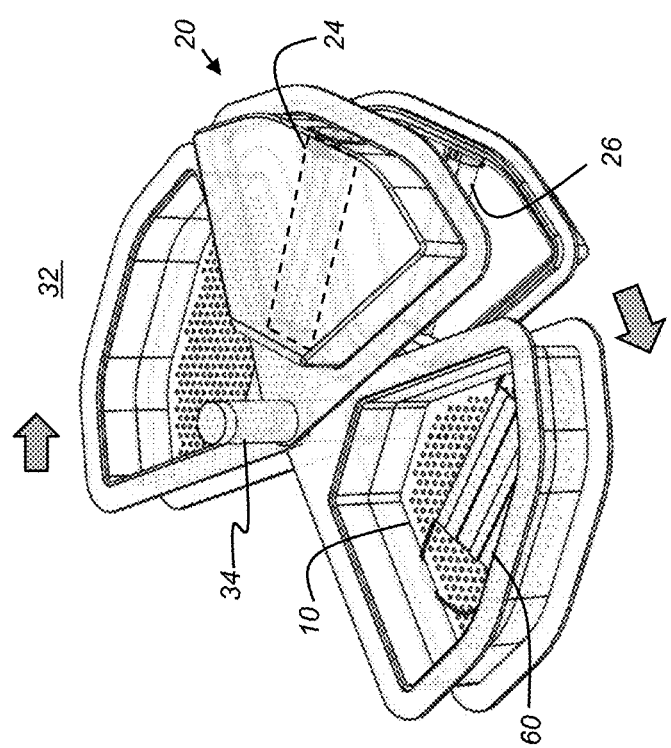
Figure 3C:
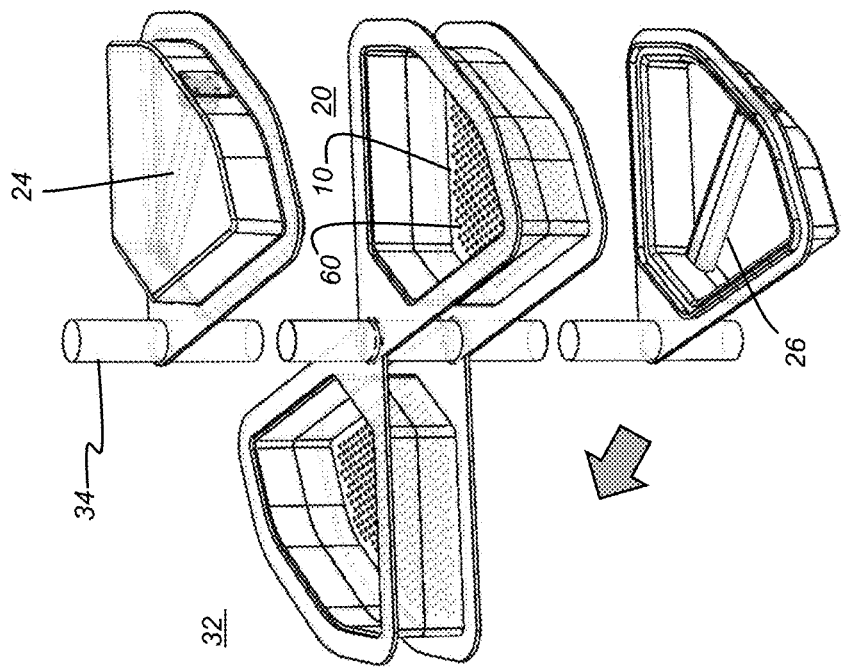
Figure 3B:
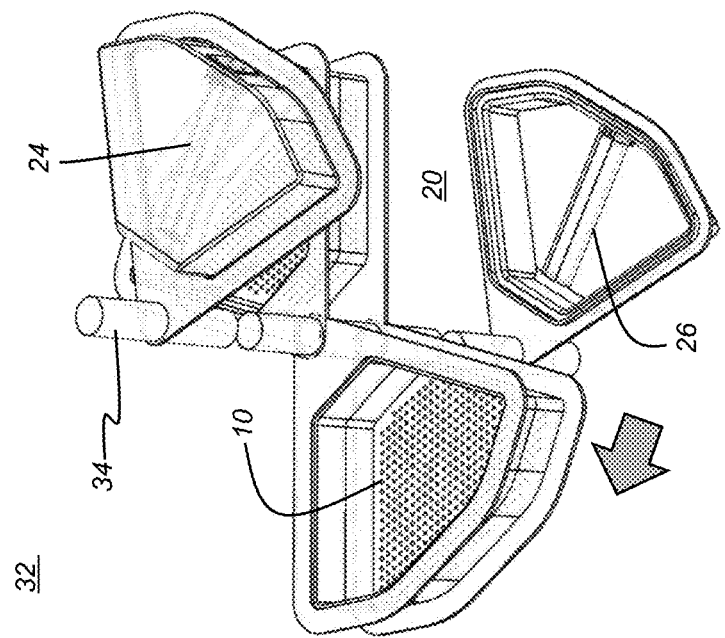
Figure 3D:
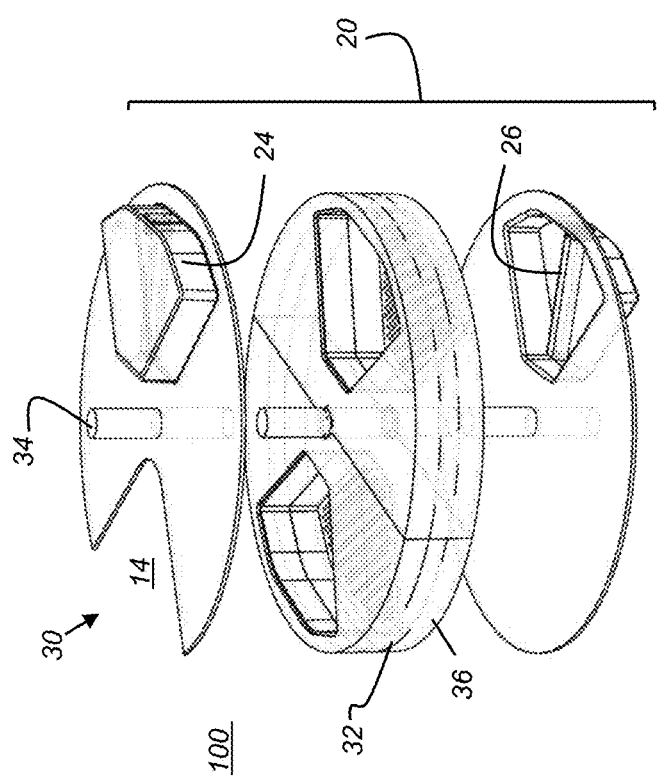

FIG. 3A shows a schematic view of exposure chamber 20 with platen 10 rotating clockwise, before the article on article support 60 on platen 10 has reached the exposure chamber 20. FIG. 3B is an exploded view at a rotational angle near that of the FIG. 3A view, showing features of carousel 32, rotating on a drive shaft 34 that serves as a pivot. FIG. 3C shows an exploded view of carousel 32 and chamber 20 components, wherein article support 60 for exposure has rotated to within the boundaries of exposure chamber 20, for exposure between upper and lower radiant energy sources 24 and 26, respectively. FIG. 3D shows an alternate exploded view of indexing apparatus 30, with shroud 36 shown in position.

FIG. 4A is an overhead schematic diagram for an embodiment that shows how the fixed sectors of the enclosure hood 16 cooperate with the revolving sectors of carousel 32 during the exposure cycle, passing the article through exposure chamber 20 long enough to deliver the needed radiant energy, while shielding the operator O from exposure throughout the cycle.

The sequence beginning in FIG. 4A and continuing through FIG. 4B shows twelve steps of the cycle, with relative component positions at successive 30-degree increments. At the 0-degree (or 360 degree) position at upper left in FIG. 4A, the relative, fixed position of hood 16 is represented, with features hidden beneath hood 16 represented in dashed lines. For the representation of subsequent angular positions, hood 16 is not shown, to allow better visibility of the hidden features. Significantly, throughout the rotation cycle, there is, except for loading and unloading the article at load station 14, no contact needed by the operator/user. There is no direct operator access to the exposure chamber 20. Exposure radiation is limited to exposure chamber 20, due to the protective configuration and rotation of sealing shroud 36, according to the embodiment shown.

As FIG. 4A shows, operator load station 14 is within a sector of the travel path that lies opposite exposure chamber 20, with respect to pivot location P, which can be shaft 34 as described previously. An operator O is represented at load station 14 in the sequence of FIGS. 4A-4B.

An article A is loaded onto article support 60 on platen 10 at load station 14 with the carousel indexed to the 0° position shown in FIG. 4A. Exposure processing and indexing apparatus 30 actuation begin with platen 10 rotation and is initiated by a signal, which may be explicitly provided by the operator O, such as by an operator action or voice command, or may be detected by sensors on apparatus 100. Apparatus 100 may run continuously in some environments, with platen 10 in continuous rotation and radiant energy sources 24, 26 continuously energized; this can be a possible solution for high-volume use, such as in an airport or other public place. Auxiliary functions, such as air cleansing, can also be provided by apparatus 100 during idle time, that is, when not actively exposing an article A, with platen 10 either continuing to rotate or paused.

Rotation of carousel components in the FIG. 4A-4B sequence is shown in the clockwise direction by way of example, not by way of limitation. At the 30° position of the carousel platen 10, article A can be at least partially under hood 16, but is not yet within exposure chamber 20. At the 60° position, support 60 is passing from operator sight at load station 14 as shroud 36 rotates with platen 10. At the 90° position, an edge of shroud 36 covers or blocks the sector previously considered load station 14 when in position before operator O. Article A has advanced toward exposure chamber 20. By the 120° position, platen 10 has advanced article A to just within exposure chamber 20, conveying article A between radiant energy sources 24 and 26 as described previously. Exposure continues through the 150°, 180°, 210°, and 240° positions. By the time carousel rotation reaches the 270° position, exposure of article A is completed. Indexing to higher angles brings article A, exposed and sanitized, back to load station 14 for removal by the operator O.

A number of observations can be made from the sequence, as described:

(i) continuous shielding of the radiant energy. At each point in the carousel rotation cycle, sealing shroud 36 or other light-blocking element fully shields the operator O from exposure to UV light from radiant energy sources 24 and 26. In the embodiment shown, operator protection can be accomplished by energy blocking using features of the rotating carousel and, optionally, also of the equipment hood 16 and other features of the apparatus, without the need to de-energize the radiant energy sources at any point during the exposure cycle. As noted previously, maintaining continuous levels of current to the radiant UV source within the enclosure can help to extend bulb life.

(ii) Radiant energy sources 24 and 26 can be continuously energized during and between cycles. As long as hood 16 and the other portions of the enclosure are in place, there is no need for extensive interlocks to prevent operator exposure in normal operation. Alternately, one or both sources 24 and 26 can be individually enabled or disabled at different points in the rotation.

(iii) Rotational speed determines exposure dose. For those angles at which article A is exposed, the speed of platen 10 rotation within the exposure chamber 20 determines the amount of exposure time and is, therefore, one significant factor in determining how much exposure is obtained. According to an embodiment, the operator can adjust exposure level by adjusting a rotational speed setting for platen 10.

(iv) Rotational speed can be varied at points during the cycle, such as to index more quickly during those parts of the rotation cycle when neither exposure occurs nor loading/unloading can take place. Thus, for example, considering the sequence of FIGS. 4A and 4B, rotation may advance platen 10 more quickly to the 90° position, then index more slowly, or momentarily stop, when at rotation angles where exposure energy is being applied to article A. The rotation speed may even be momentarily adjusted to 0 if desired, resulting in one or more static exposure periods during the decontamination cycle. Rotation direction can also be controlled. For example, platen 10 can be configured to change its rotation direction before, during, or following exposure.

(v) Although 90-degree quadrants are primarily shown in the example systems described herein in detail, other sector arrangements are possible, applying the same teachings used herein for confining the radiant energy to exposure chamber 20 and shielding the external loading area and operator O over the full rotation of the carousel 32. For example, a system can provide multiple platen 10 sectors for loading articles to be exposed, separated from each other by wedge or panel sections or sectors of sealing shroud 36. The platen 10 sectors could occupy less than a 90-degree quadrant. Sealing shroud 36 portions could similarly be reduced in angular extent (arc length) from the 90-degree sector arrangement shown herein, and can be supplemented with an arrangement of seal features that are stationary or that travel with carousel 32. Exposure chamber 20 can be a sector of different size than is shown herein, extending over a shorter or longer arc length (thus, active for less or more of the travel path); alternately, multiple exposure chambers 20 could be provided, with similar or with different intensities and wavelengths. An arrangement of stationary seals can be provided, blocking stray light from reaching load station 14.

(vi) Platen 10 can be outfitted with various types of article support 60 retaining devices for holding different types of personal articles for exposure.

For example, article support 60 could include a holder configured for seating a cell phone or a laptop computer.

By way of example, FIGS. 5A and 5B show an alternative arrangement of exposure apparatus 100 wherein carousel 32 has stationary seal areas 50 and a larger exposure chamber 20 that covers an approximately 180° sector. Multiple platen 10 sectors can act as loading areas for user articles. FIGS. 5C and 5D are perspective views showing relative positions of the rotated carousel 32 to stationary components according to an embodiment.

Configuration of Platen 10

The perspective view of FIG. 2B shows an arrangement of platen 10 with a load station 14 defined by edges of shroud 36 as light-blocking features. Shroud 36 can be formed by any suitable material that sufficiently blocks UV or other radiation from sources 24, 26.

Platen 10 can be a material that is transparent to the radiation wavelengths, such as a glass having high UV transmission or a mesh material. Platen 10 can be perforated to improve radiation transmission. Platen 10 can be formed as a single disk or can be ribbed or formed in sections.

Stationary Seals for Light Containment

In addition to the rotary seal provided by sealing shroud 36, apparatus 100 can also have an arrangement of stationary seals that work in cooperation with the sealing shroud 36 as it rotates throughout its angular positions.

FIG. 6 is a perspective view, with carousel platen 10 removed, showing components forming a base covering 40 of the exposure carousel housing and bottom surfaces of the exposure chamber 20. Lower radiant energy source 26 is positioned beneath the support surface for the article, such as within a well 44 formed in the housing, as shown. Seals 42 are disposed to seat against the lower surfaces of sealing shroud 36 as it rotates past, thereby preventing light leakage from within base covering 40. Similar seals, not shown, can also be coupled to hood 16 for blocking leakage of radiant energy above platen 10. Arrows represent a rotation direction. Rotation in the alternate direction can be used.

As shown in FIG. 7, additional stationary perimeter seals 46 are vertically disposed to block radiant energy leakage from along moving edges of shroud 36.

FIG. 8 shows sealing shroud 36 in position relative to seals 42 and 46 for confining exposure radiation to the exposure chamber throughout platen 10 rotation.

Timing Example

The graph of FIG. 9 shows an exemplary timing chart for various phases of operation of apparatus 100, with the sequencing of processes that can be executed during the exposure cycle. The processing sequence tracks the rotation angle of the carousel platen 10, as was described previously. Motor speed varies from stopped, to an indexing speed, to an exposure speed during processing. Indexing speed can be at the highest revolutions-per-minute (RPM), with exposure speed at a fraction of the indexing speed, such as half, for example. In the FIG. 9 process, the motor is stopped until pressing of a foot pedal or other switch actuates the motor to initiate the exposure cycle; alternately, the motor can be continuously running, such as at a lower speed suitable for exposure. Briefly stopping motor actuation allows time for loading platen 10.

The exposure radiant energy source can be continuously energized or can be turned off until after cycle initialization. Air flow, or introduction of a neutral gas or other gas or vapor material, can be varied on or off, depending on the phase of the cycle being executed. In the FIG. 9 example, the air flow is turned OFF during exposure; however, this may not be the preferred method in other embodiments. An indicator, such as an indicator light or button on a display screen, can show the various parts of the cycle. For the example shown in FIG. 9, indicators can display Load, Index, Expose, and Unload status of the exposure process.

As the example timing sequence of FIG. 9 shows, embodiments of the present disclosure can allow user adjustment or programming of different functions, such as timing of air flow, motor speed, exposure energization, and the like. A graphical user interface can also show, in animated form, the current status of the apparatus, including visual indication or map that shows the location of user articles being processed beneath the hood.

According to an alternate embodiment of the present disclosure, UV exposure apparatus 100 can also be employed for cleansing of the ambient air under UV light, such as by directing an air flow through hood 16. Apparatus 100 can provide a ventilation path for sustained or controlled intake, exposure, and release of ambient air. Ventilation openings and one or more optional fans can provide a continuous or periodic flow of air into exposure chamber 20, thus allowing the UV radiation to destroy airborne pathogens as well as those found on surfaces of personal articles. According to an alternate embodiment of the present disclosure, the air cleaning function operates primarily when apparatus 100 is idle; however, simultaneously cleaning the surrounding air and cleaning personal articles can have clear advantages for more thorough decontamination at a site.

Expanding the Number of Load and Article-Support Sectors

The movement progression diagrams of FIGS. 4A and 4B showed the processing sequence for apparatus 100 having a single fixed load station 14 and corresponding sector for placement of articles to be exposed, and two movable article-support sectors of the carousel that align with the fixed load station 14 for article loading and removal. Alternate embodiments allow an expanded number of fixed sectors of the enclosure for loading and exposure as well as movable sectors on the rotating carousel 32 for article support, provided that operator exposure is prevented during all phases of the exposure cycle, at all rotational angles of carousel 32.

FIGS. 10A-10C show the stationary exposure chamber (represented by the solid outer circle), and a number of fixed sectors defined within the enclosure for exposure apparatus 100: the load sector 58 (vertical hashed region), two seal sectors 54 and 56 that bound the load sector 58, and the exposure sector 64 that forms exposure chamber 20 (horizontal hash region). Each of these fixed sectors has an angular span associated with it: $\theta_L$, $\theta_S$, and $\theta_E$, respectively. It is assumed that the exposure chamber 20 itself has at least a top, a bottom, and an outer circumferential side. These form the outer surface contacted by the seals 42, 52, 62, and 72. There is also movable, rotating carousel 32 represented by the dashed inner circle in FIG. 10A and shown with its movable sectors at different rotations in FIG. 10B. Carousel 32 rotates one or more movable article-support sectors 80 and one or more movable energy-blocking sectors 90. Each article-support sector 80 is flanked by edges of the energy-blocking sectors 90. The energy-blocking sector surfaces form the inner surface that provides energy-blocking features contacted by the seals.

Angular spans for the different sectors and for seal positioning follow a number of guidelines, including the following:

(i) Requirements are based on the choice of particular chamber load sector angular span $\theta_L$ and carousel article-support sector angular span, which is assumed to also be at least approximately equal to $\theta_L$ for typical configurations.

(ii) The fixed chamber load sector 58 is flanked by two fixed chamber seal sectors 54, 56, and movable carousel article-support sectors are flanked by movable carousel energy-blocking sectors. For a typical configuration, we assume there is one load sector (though there could be more than one), but there are typically more than one article-support sector.

(iii) The seals provide a light-tight seal for the enclosure in the following regions: below the top of the chamber and above the tops of the energy-blocking sectors of the carousel; inside the side of the chamber and outside the sides of the energy-blocking sectors of the carousel; and above the bottom of the chamber and below the bottoms of the energy-blocking sectors of the carousel. The seals may be attached to either the chamber or the energy-blocking sectors of the carousel, and can slide or brush against the contacting surface that moves along the seal.

(iv) The seal sector angular span $\theta_S$ must be greater than or equal to the load sector angular span $\theta_L$ in order to prevent UV light from escaping the exposure area: $\theta_S \geq \theta_L$.

(v) The carousel can accommodate up to N article-support sectors of angular size $\theta_L$, wherein:

$$N = \text{floor}(360°/\theta_L).$$

By definition the floor function rounds down the value upon which it operates to the nearest integer. For example, if $\theta_L = 90°$, N=4; if $\theta_L = 60°$, $N_{max} = 6$; and if $\theta_L = 50°$, $N_{max} = 7$.

To achieve the maximum value of N, the energy-blocking sectors must span the minimum possible range, or approximately 0°. For many of the embodiments shown, including that in FIGS. 10A and 10B, the energy-blocking sectors are chosen to be larger for design reasons, and as a result there may be accordingly fewer article-support sectors (N<$N_{max}$).

(vi) The chamber exposure sector may be as large as the angular span which remains after excluding the load sector and the two seal sectors. The exposure sector angular span is thus given by:

$$\theta_E = 360° - \theta_L - 2\theta_S.$$

For a given $\theta_L$, the maximum $\theta_E$ occurs when $\theta_L = \theta_S$, which results in $\theta_{E,max} = 360° - 3\theta_L$.

As an example, if $\theta_L = \theta_S = 60°$, $\theta_{E,max} = 180°$. If $\theta_L = 55°$ and $\theta_S = 65°$, then $\theta_E = 175°$. This case is illustrated in FIGS. 10A, 10B.

Based on the arrangement of FIG. 10A, FIG. 10B provides an illustration, for different carousel rotation angles, of how the rules stated herein apply wherein $\theta_L = 55°$, $\theta_S = 65°$, and N=3, as shown. As noted, in this case $\theta_E = 175°$. The condition at each of a number of angles in FIG. 10B is given as follows:

(1) Carousel at 0°:
Carousel article-support sector 80 is aligned with stationary chamber load sector 58.
There are two other movable carousel article-support sectors, both of which are within the fixed chamber exposure sector.
UV light in the chamber exposure sector is prevented from escaping the chamber by the seals 42, 52, 62, and 72, which make contact between the carousel energy-blocking sectors 90 which flank article-support sector 80 and the chamber seal sectors 54 and 56 which flank load sector 58.

(2) Carousel at 30°:
Carousel article-support sector 80 is partially in the chamber load sector 58, and partially in the chamber seal sector 40.
UV light in the chamber 20 of exposure sector 64 is prevented from escaping the chamber by at least two seals 42 and 62 which contact the carousel energy-blocking sectors 90 and chamber seal sectors 54 and 56.

(3) Carousel at 60°:
Carousel article-support sector 80 is now fully within the chamber seal sector.
UV light in the chamber exposure area is prevented from escaping the chamber by the four seals 42, 52, 62, and 72, which make contact between the carousel energy-blocking sectors 90 and the chamber seal sectors.

(4) Carousel at 90°:
Carousel article-support sector 80 is partially in the chamber seal sector 54, and partially in exposure sector 64.
UV light in the chamber exposure sector is prevented from escaping the chamber by two seals 52 and 72 which contact the carousel energy-blocking sectors and chamber seal sectors.

(5) Carousel at 120°:
Carousel article-support sector 80 is now fully within the chamber exposure sector 64.
UV light in the chamber exposure area is prevented from escaping the chamber by the four seals which make contact between one of the carousel energy-blocking sectors and the chamber seal sectors.

FIG. 10C shows, from a top schematic view, some of the geometric relationships that constrain angular span in various configurations. The two figures show a load sector L with corresponding angle $\theta_L$, an exposure sector E with corresponding angle $\theta_E$, and two light-blocking seal sectors S or K with corresponding angle $\theta_S$ that bound the load sector L.

Operator Controls and Feedback

Embodiments allow the operator to initiate exposure in a number of ways. According to one embodiment, a foot pedal can be provided on, or connected through, the apparatus 100 pedestal. Alternately, a switch or sensor can be provided to respond to other operator input. Sensors can be used to detect operator placement of the article at the loading station and removal of operator hands from the station.

According to an alternate embodiment, a camera can be provided for capturing image content related to the operator. A clear operator gesture or movement can be interpreted as an initiation instruction.

A microphone can be used to detect an audible instruction to begin exposure.

According to an embodiment, trained logic can be employed to interpret operator movement and/or voice input and to initiate system operation based on learned gestures, voice patterns, or other input or combination.

The amount of exposure energy can be varied by changing the rotational speed of platen 10 during exposure of the article. A speed control, as well as controls for various patterns of exposure current, pulsing, timing, use of one or both sources or alternating source energization, and source/movement synchronization can be provided in order to vary how much exposure dose is delivered to article surfaces. Controls can be provided in a recessed area of hood 16 or at some other appropriate location on the apparatus.

According to an alternate embodiment, visual indication of exposure progress can be provided by providing filtered light output through one or more windows 48 in side surface 18. Windows 48 can include a filter element that blocks harmful spectral content and transmits residual blue or other light emitted from the radiant energy sources.

According to another alternate embodiment, a camera can be disposed within exposure chamber 20 and is in signal communication with a display that is mounted on hood 16 or other surface. Use of the camera and display allows the operator to view the exposure process as it occurs.

A display can be provided on the operator interface to show approximate cycle time elapsed.

Various types of sensors can be provided to measure exposure levels and to provide one or more signals that can be used for reporting and adjustment of exposure intensity or timing, for example.

The apparatus 100 can be network-connected in order to provide information on internal operation, parts processed, and other performance data. In addition, network connection allows software upgrade and other features for operator information and convenience.

In embodiments described and illustrated herein, the transport path for exposure of the article is shown in a generally horizontal plane. According to an alternate embodiment, apparatus 100 can provide a transport path that is vertical, or at some other angular orientation. It may be advantageous for some articles to change the rotational angle of the transport path, such as for orienting the article at different angles in one or more revolutions of the carousel.

The invention has been described in detail with particular reference to a presently preferred embodiment, but it will be understood that variations and modifications can be effected within the spirit and scope of the disclosure. The presently disclosed embodiments are therefore considered in all respects to be illustrative and not restrictive. The scope of the invention is indicated by any appended claims, and all changes that come within the meaning and range of equivalents thereof are intended to be embraced therein.

The invention claimed is:

1. An apparatus for exposing an article to radiant energy, comprising:
   a carousel configured to rotate about an axis and having an article support in a support circular sector defined between a first energy-blocking radially extending wall of the rotating carousel and a second energy-blocking radially extending wall of the rotating carousel,
   wherein each energy-blocking radially extending wall joins a curved energy-blocking outer wall to define an energy-blocking circular sector;
   an actuator energizable to rotate the carousel and to revolve the article support along a circular transport path;
   an enclosure having a stationary hood that defines an enclosed circular sector of the transport path and an unenclosed circular sector of the transport path;
   and at least a first radiant energy source energizable to direct the radiant exposure energy toward the carousel along the enclosed circular sector of the transport path,
   and wherein the curved energy-blocking outer wall rotates with the first and second energy-blocking radially extending walls of the carousel to block leakage of the radiant energy from the enclosed circular sector of the transport path throughout a full rotation of the carousel.

2. The apparatus of claim 1 wherein the radiant exposure energy includes ultraviolet light.

3. The apparatus of claim 1 wherein the article support comprises a glass material.

4. The apparatus of claim 1 wherein the article support comprises a substantially transparent mesh.

5. The apparatus of claim 1 wherein the first and second energy-blocking radially extending walls are formed of a polymer.

6. The apparatus of claim 1 further comprising a second radiant energy source, wherein at least a portion of the enclosed sector of the transport path extends transversely between the first and second radiant energy sources.

7. The apparatus of claim 1 further comprising one or more stationary seals for blocking the radiant exposure energy, wherein the one or more stationary seals are coupled to the enclosure.

8. The apparatus of claim 1 further comprising a speed control for adjusting carousel rotation speed.

9. The apparatus of claim 1 wherein the article support is a first article support and wherein the rotating carousel further comprises a second article support that is configured to revolve along the circular transport path.

10. The apparatus of claim 1 wherein the apparatus further comprises a ventilation path for intake, exposure, and release of ambient air.

11. An apparatus for exposing an article to radiant energy, comprising:
    (a) an exposure chamber having an upper radiant energy source and a lower radiant energy source within a hooded enclosure; and
    (b) a rotary exposure carousel driven by an actuator and configured for rotating about an axis and indexing the article, along a circular transport path centered about the axis, from a loading station, through the enclosed exposure chamber, transversely between the upper and lower radiant energy sources, and back to the loading station, wherein, with respect to a plane perpendicular to the axis of rotation and defined by the transport path, the upper and lower radiant energy sources are disposed on opposite sides of the plane,
    wherein the rotary exposure carousel further indexes along the transport path one or more energy-blocking circular sectors, each energy-blocking circular sector comprising a first and a second energy-blocking side wall, both energy-blocking side walls extending outward from the axis in a radial direction, and both energy-blocking side walls intersecting with a curved energy-blocking outer wall that extends across the energy-blocking circular sector in an arc that is concentric with the axis,
    and wherein, throughout a complete rotation of the carousel, each energy-blocking sector maintains a continuous energy-blocking seal against the hooded enclosure that blocks leakage of the radiant energy from the exposure chamber.

12. The apparatus of claim 11 wherein at least the upper radiant energy source emits ultraviolet light.

13. The apparatus of claim 11 wherein the light-blocking side walls are formed of metal.

14. The apparatus of claim 11 wherein the hooded enclosure further comprises a control panel and a display.

15. The apparatus of claim 11 wherein the loading station lies opposite the exposure chamber with respect to the axis.

16. A method for exposing an article to radiant energy, comprising:
    (a) providing a carousel having an axis of rotation and at least one article support, wherein the at least one article support is defined within a support circular sector of the carousel that lies between a corresponding pair of energy-blocking radially extending walls of the carousel,
    and wherein the energy-blocking radially extending walls join a curved energy-blocking outer wall that lies along an arc that is concentric with the axis of rotation and defines an energy-blocking circular sector of the rotatable carousel;

(b) exposing the article by rotating the carousel within an enclosure having a stationary hood that defines an enclosed circular sector and an unenclosed circular sector, indexing the article support about the axis of rotation along a circular transport path from an article loading position, wherein the support circular sector is aligned within the unenclosed circular sector, then through a continuous angular range that extends over a plurality of exposure positions, with the support circular sector moving within the enclosed circular sector of the stationary enclosure; and (c) energizing one or more light energy sources that direct radiant energy toward the carousel over the angular range of exposure positions, wherein the pair of energy blocking radially extending walls, curved energy-blocking outer wall, and stationary enclosure continuously block the radiant energy from leakage from the enclosed circular sector at all angles during full rotation of the carousel.

17. The method of claim 16 wherein the one or more light energy sources remain energized at every rotational angle of the carousel along the circular transport path.

18. The method of claim 16 further comprising directing a forced-air flow through the hood.

19. The method of claim 16 further comprising introducing a fluid into the hood during carousel rotation.

20. The method of claim 16 further comprising providing an operator control setting for adjusting actuator speed.

* * * * *